Figure 1:
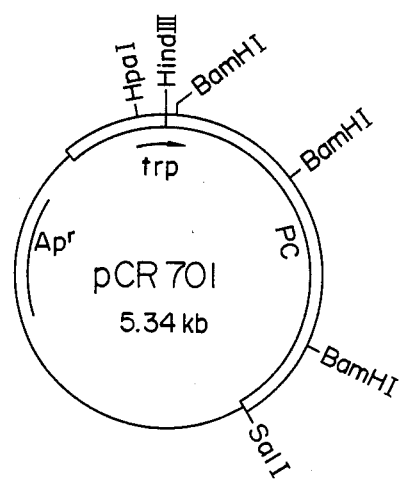

United States Patent [19]

Beppu et al.

[11] Patent Number: 4,757,020
[45] Date of Patent: Jul. 12, 1988

[54] NOVEL EXPRESSION PLASMIDS CONTAINING THE FULL CDNA SEQUENCE OF CALF PROCHYMOSIN

[75] Inventors: Teruhiko Beppu, 5-21, Horinouchi-1-chome, Suginami-ku, Tokyo; Takeshi Uozumi; Katsuhiko Nishimori, both of Tokyo; Norio Shimizu, Hitachi; Yoshiyuki Kawaguchi, Tokyo; Noboru Yanagida, Yokohama, all of Japan

[73] Assignee: Teruhiko Beppu, Tokyo, Japan

[21] Appl. No.: 706,979

[22] Filed: Mar. 1, 1985

[30] Foreign Application Priority Data

Mar. 9, 1984 [JP] Japan ................... 59-44901

[51] Int. Cl.[4] ............... C12N 1/20; C12N 15/00; C12N 1/00
[52] U.S. Cl. ................... 435/253; 435/172.3; 435/320; 935/44; 935/45
[58] Field of Search ........... 435/172.3, 253, 68, 435/317, 320; 935/44, 45

[56] References Cited

FOREIGN PATENT DOCUMENTS 57350 8/1982 European Pat. Off. .
68691 1/1983 European Pat. Off. .

OTHER PUBLICATIONS

Nishimori et al, Gene, vol. 19, pp. 337-344, 1982.
Goff et al, Gene, vol. 27, pp. 35-46, 1984.
Fujisawa et al, Nuclei Acids Research, vol. 11, pp. 3581-3591, Jun. 1983.
Tacon et al, Molec. Gen. Genet., vol. 177, pp. 427-438, (1980).
Guarente et al, Cell, vol. 20, pp. 543-553, Jun. 1980.
Roberts et al, PNAS U.S.A., vol. 76, pp. 760-764, Feb. 1979.
Maniatis et al, Molecular Cloning, A Laboratory Manual, Cold Spring Harbor Lab., pp. 411-417, (1982).
Abstract of the Japanese Agricultural Chemistry Society Meetings, 2A-19 (1983).

Primary Examiner—Alvin E. Tanenholtz
Attorney, Agent, or Firm—Wegner & Bretschneider

[57] ABSTRACT

Expression plasmids containing the full cDNA sequence of calf prochymosin and capable of expressing prochymosin gene in *E. coli* host cells are disclosed. A method is described for the preparation of said plasmids which comprises altering the spacing between the SD and ATG sequences within the *E. coli* trp promoter-operator region of the parent expression plasmid, pCR 701, which is known to express prochymosin gene in the *E. coli* host cells. These modified expression plasmids are designed to provide high expression levels of prochymosin.

3 Claims, 2 Drawing Sheets

NOVEL EXPRESSION PLASMIDS CONTAINING THE FULL CDNA SEQUENCE OF CALF PROCHYMOSIN

This invention relates to recombinant expression plasmids capable of expressing prochymosin gene. More particularly, it relates to novel expression plasmids containing the full cDNA sequence of calf prochymosin and capable of efficiently expressing the full-length cDNA in *E. coli* host cells under the control of the *E1 coli* trp promoter.

Prochymosin is secreted by the calf fourth stomach (abomasum), and is a precursor protein of chymosin which is responsible for coagulating milk in the manufacture of cheese. Prochymosin has a molecular weight of about 40,000, and consists of 365 amino acid residues. A peptide consisting of 42 amino acids was cleaved from the N-terminus of prochymosin by selfdigestion, resulting in the formation of cymosin. Recently milk-coagulating enzymes, of microbial origin, have been discovered and these are substituting for chymosin. Nevertheless, the need still exists for calf prochymosin in the cheese industry. Accordingly, it has been considered one of the primary objectives in the application of Genetic Engineering to utilize the recombinant DNA technology and to have microorganisms produce the calf prochymosin.

It is one objective of this invention to provide novel expression plasmids capable of realizing the expression of the full-length cDNA of prochymosin with high expression levels under the control of *E. coli* trp promoter.

It is another objective of this invention to provide methods for the production of prochymosin which comprises transforming host organisms with the above-stated expression plasmids and growing the thus-obtained transformants.

It is a still further objective of this invention to provide methods for the construction of the above-stated expression plasmids.

By employing the recombinant DNA technology, prochymosin cDNA is made to express by transformation in *E. coli* host cells, and then to produce prochymosin within the cells; this method is known to those skilled in the art. For example, the production of prochymosin under the control of the *E. coli* lac operon promoter is described by Nishimori et. al., Gene, 19, 337 (1982) as well as in Japan Kokai 58-32,896 (to Teruhiko Beppu) and Japan Kokai 57-141,287 (to Collaborative Research Inc.). Similarly, under control of the *E. coli* trp promoter, prochymosin is produced. This is reported by Shimizu et. al., Abstracts of the Japanese Agricultural Chemistry Society Meetings, 2A-19 (1983), and in Japan Kokai 58-9,687 (to Cell Tech. Ltd.) and Japanese Appln. 58-38,439 (to Teruhiko Beppu). Particularly, the cited Shimizu reference discloses plasmids pCR 701 containing the cloned full-length structural prochymosin gene as well as the expression of said plasmid in *E. coli* host cells under the control of the *E. coli* trp promoter. This plasmid, in its full length, comprises about 5.3 Kb and has the insert of the full-length prochymosin cDNA at the ribosome binding site of the trp L gene downstream from the trp promoter. For reference, the restriction map of pCR 701 is shown in FIG. 1. There are 14 bases between the SD sequence and the ATG codon, namely:

5'—AAGGGTATCGATAAGCTTATGGCT——3'

SD                   Met Ala prochymosin

*E. coli* c 600 $r_k^- m_k^-$ (PCR 701), transformed with this plasmid, has been deposited with the FRI (Fermentation Research Institute) as Accession No. FERM-BP-264. Nevertheless, as stated in the Nishimori reference, the expression level of pCR 701 is much lower than those of other known plasmids such as pCR 501 and pCR 601. Its production level of prochymosin protein is, as determined by the competitive radioimmunoassay method, about 700 molecules per host cell, while according to the immunoblotting methd the level is about 12,000 molecules per host cell.

In one aspect of this invention there is provided a recombinant expression plasmid comprising the full cDNA sequence of prochymosin and an *E. coli* trp promoter-operator system and capable of expressing the full-length cDNA of prochymosin under the control of the trp promoter, characterized in that an ATG initiation codon is joined to the N-terminus of said cDNA and the base pairs between the SD sequence and the ATG initiation codon within said promoter region are constructed so as to give high expression levels.

In another aspect of the invention there is provided a method for the preparation of novel plasmids with high expression efficiency which comprises slicing by restriction enzymes the base sequence of pCR 701 between the SD sequence and the ATG codon; ligating the cut ends; and thereby altering the constitution of the base pairs between said SD and ATG sequences (e.g., the arrangement of base pairs and/or the number of intervening base pairs).

In this method, it is possible to lengthen the spacing between the SD sequence and the ATG initiation codon by cleaving with restriction enzymes, repairing the resultant single-stranded termini, and ligating the cut ends. Conversely, it is also possible to shorten said spacing by removing the single-stranded termini and ligating the cut ends. Preferably, the latter method (i.e., shortening the spacing) is employed in this invention.

In another aspect of this invention there is provided a process for the production of prochymosin comprising the steps of introducing the herein-described plasmids that have high expression levels into a host microorganism by transformation and cultivating the transformed host cells.

Also included in this invention are the above transformed host microorganisms and prochymosin produced by them.

Any microorganism capable of accepting, replicating the expression plasmids constructed by the processes of this invention, and producing prochymosin upon propagation of cells can be used as a host microorganism but; for practical reasons, *E. coli* c 600 derived strains are preferably used in this invention. Particularly preferred strain is *E. coli* c 600 $r_k^- m_k^-$.

The prochymosin produced by a process according to this invention may be methionylprochymosin having methionine at the N-terminus of prochymosin but may simply be referred to as prochymosin throughout the Specification.

Figure 2:
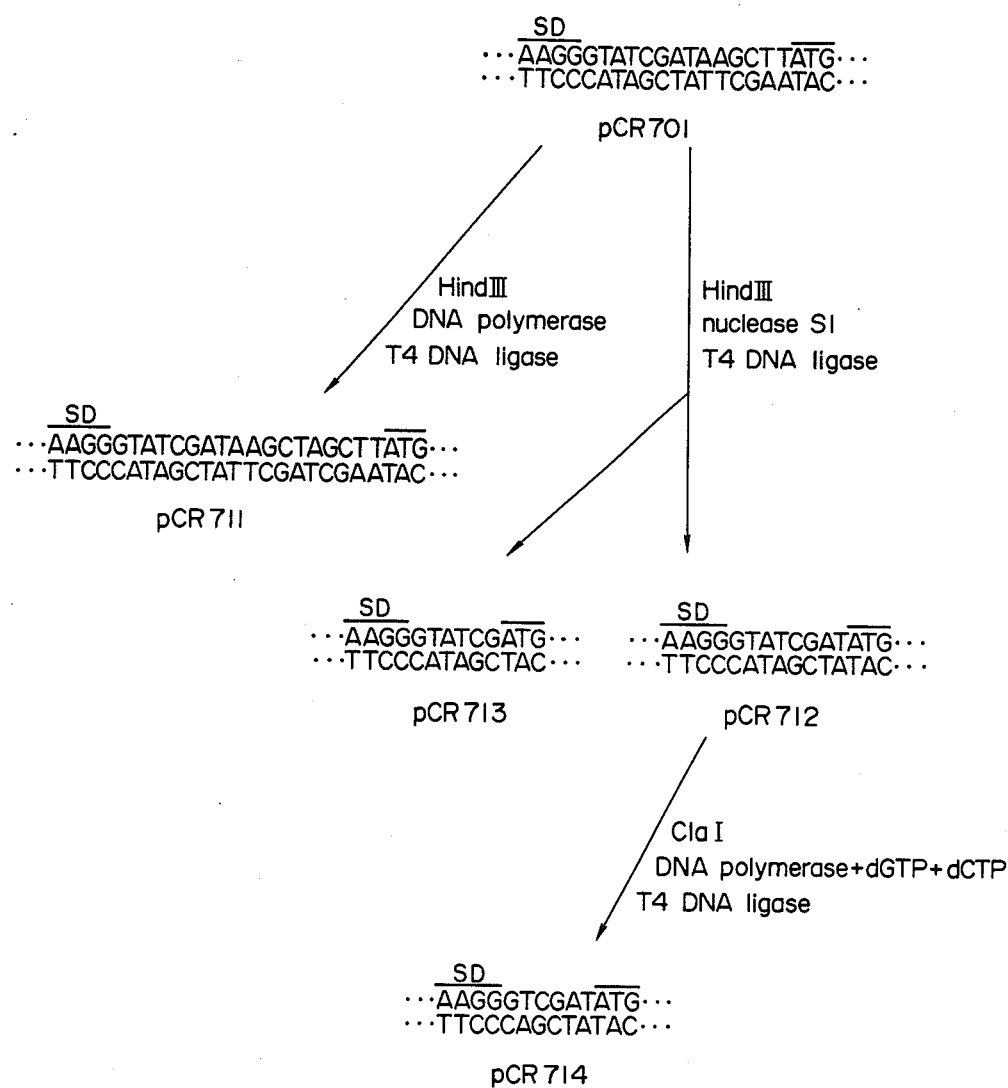

In the Drawings, FIG. 1 shows a restriction enzyme map of pCR 701. FIG. 2 shows a flow chart for the construction of recombinant plasmids, pCR 711, pCR 712, pCR 713, and pCR 714, beginning with the parental plasmid pCR 701; and base sequences between the SD sequence and the ATG initiation codon for each plasmid.

This invention will be described in more detail by referring to preferred embodiments.

Plasmid pCR 711

Plasmid pCR 701 is digested with HindIII. The resultant single-stranded portions at both cut ends are repaired by means of DNA polymerase. The resultant blunt ends are ligated together by T4 DNA ligase. After these operations the spacing between the SD and the ATG initation codon is increased by 4 base pairs to become 18 base pairs. The thus-produced plasmid, designated pCR 711, is identical with pCR 701 except the base sequence between the SD sequence and the ATG codon. the DNA sequence of this plasmid in the region between them, as analyzed according to the method of Maxam-Gilbert, is:

Construction of pCR 711 from pCR 701 is schematically represented in FIG. 2.

$E.$ $col$ c 600 $r_k^-m_k^-$ strain is transformed with pCR 711 by standard procedures and amplicillin resistant clones are selected. These clones are all found to have pCR 711 plasmid and will produce prochymosin under the control of the trp promoter.

Plasmid pCR 712 and Plasmid pCR 713

As previously described for pCR 711, plasmid pCR 701 is digested with HindIII. The resultant single-stranded ends are removed by nuclease S1. The thus-obtained blunt ends are ligated together by T4 ligase. By varying the conditions for digestion with Nuclease S1 (namely, composition of the buffered solutions), plasmid pCR 712 or pCR 713 is produced respectively. Both plasmids differ from each other in the distance between the SD and ATG sequences, but are identical with pCR 701 except said distance.

The DNA sequence of pCR 712 in the region between the SD and the ATG initiation codon, as analyzed according to the method of Maxam-Gilbert, is:

In like manner, the corresponding DNA sequence of pCR 713 is analyzed to be:

Construction of pCR 712 or pCR 713 from pCR is schematically represented in FIG. 2. Among host cells transformed with pCR 712, amplicillin resistant clones are selected. These clones are all found to have pCR 712 and will produce prochymosin under the control of the trp promoter.

A transformant, designated as $E.$ $coli$ c 600 $r_k^-m_k^-$ (pCR 713), which carries pCR 713 will also produce prochymosin.

Plasmid pCR 714

Plasmid pCR 712 is digested with claI. The resultant single-stranded portions at cut ends are partially repaired by DNA polymerase in the presence of dGTP and dCTP. When only the CG site is repaired and the partially repaired ends are ligated by means of T4 DNA polymerase, plasmid pCR 714 is produced. After these operations, the number of base pairs between the SD sequence and the ATG codon is reduced by 2 base pairs to become 6 pairs. Except this base sequence, pCR 714 is exactly the same as pCR 712. The DNA sequence of pCR 714 in the region between the SD sequence and the ATG initiation codon, as analyzed according to the method of Maxam-Gilbert, is:

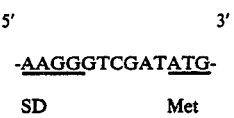

Construction of pCR 714 from pCR 712 is schematially represented.in FIG. 2.

Among host cells transformed with pCR 714, ampicillin resistant clones are selected. These clones are all found to have pCR 714 and will produce prochymosin under the control of the trp promoter.

Expression Experiments $E.$ $coli$ c 600 $r_k^-m_k^-$ transformants each containing pCR 711, pCR 712, pCR 713 or pCR 714 can be grown under conventional culturing conditions. Examples of the culture media used are the well-known L-B Broth and M-9 Broth. Cells are grown in these media to a density of $10^{12}$ cells per liter. After an appropriate period of fermentation, the cell extract is prepared. This extract is examined by the binding competitive radioimmunoassay method as well as by the protein blotting method. In both measurements, protein products have been detected and they are indistinguishable from prochymosin in terms of molecular weight and immunological properties. The production level of prochymosin for each plasmid-containing plasmid has been estimated. The pCR 712 strain has shown the highest level among those examined, which level is about 300,000 molecules per cell as determined by the protein blotting method. It is surprising that the ability of the pCR 712 transformant to produce prochymosin has been increased to approximately twenty five times that of the parent pCR 701 strain.

The prochymosin production levels of the other plasmid-containing strains are in the order of:

It is deduced from the above results that among pCR 701 derived expression plasmids the expression efficiency of prochymosin is not necessarily contigent upon the spacing between the SD sequence and the ATG initiation codon but also upon the base sequence itself. Prochymosin derived from microorganism can be activated to the active chymosin by exposure to acidic pH.

This invention will be described in some more detail by way of illustration and example; nevertheless, it should be understood that certain changes and modifications be practiced within the scope of the invention.

EXAMPLE

Throughout the following examples, "TEN buffer" is meant a buffered solution containing Tris-Hcl (20mM), NaCl (50mM) and EDTA (1mM) with a pH of 7.5.

Nutrient media for transformation and expression experiments are:

| L-Broth/1 (pH: 7.2-7.4) | |
|---|---|
| Bacto-Trypton | 10 g |
| Yeast Extract | 5 g |
| Glucose | 1 g |
| NaCl | 5 g |
| M9-Broth/1 | |
| NaHPO$_4$ | 6 g |
| KH$_2$PO$_4$ | 3 g |
| NaCl | 5 g |
| NH$_4$Cl | 1 g |
| CaCl$_2$ | 15 mg |
| MgSO$_4$.7H$_2$O | 0.1 g |
| Bl(Thiamine HCl) | 0.2 g |
| Casamino acid | 2.5 g |
| Glucose | 5 g |
| 3 β-Indolylacrylic acid | 1.5 mg |
| Ampicillin | 50 mg |

Example 1

Construction of Plasmid pCR 711

Plasmid pCR 701 was digested with HindIII by incubation at 37° C. for 2 h in a 100 μl solution containing Plasmid (10 μg in 32 μl TEN), HindIII (30 U, 5 μl TEN), HindIII buffer (5 μl) and H$_2$O (53 μl). The resultant DNA was precipitated with ethanol and dissolved in 20 μl of TEN. The digested pCR 701 was repaired at its cut single stranded portions by incubation at 30° C. for 10 min in a 40 μl solution containing Plsmid (4 μg in 8 μl TEN), DNA polymerase I (Klenow fragment) (1.5 U, 1 μl TEN), polymerase buffer (4 μl), 5mM dNTP (4 μl TEN) and H$_2$O (23 μl). The reaction was terminated by phenol treatment; phenol was removed by ether extraction; and the DNA was then precipitated with ethanol and dissolved in 20 μl H$_2$O. To this solution containing 4 μg of DNA was added T$_4$ DNA ligase (3.6 U, 4 μl TEN), 3mM ATP and x5 ligation buffer (8 μl), resulting in a final volume of 40 μl. After incubation at 22° C. overnight, the reaction was terminated; the DNA was precipitated with ethanol; and the precipitated DNA was dissolved in 40 μl TEN. Transformation of the host E. coli c 600 $r_k^-m_k^-$ was carried out in accordance with the method of Norgard (Gene, 3, 279 (1978)). The thus-prepared competent cells (i.e., capable of accepting foreign DNA) were treated with the above DNA solution to complete transformation. After the transformed cells were grown in L broth containing ampicillin (50 μg/ml), ampicillin transformants were selected. These transformants, designated as E. coli c 600 $r_k^-m_k^-$ (pCR 711), were found to contain plasmid pCR 711.

Example 2

Construction of Plasmid pCR 712

The HindIII digest of pCR 701 obtained by the procedure of Example 1 was incubated at 16° C. for 2 h in a total volume of 50 μl containing the digest (1 μg in 2 μl TEN), Nuclease S1 (50 U, 1 μl TEN), Nuclease S1 buffer (5 μl) and H$_2$O (42 μl). The Nuclease S1 buffer (x 10) contained 2.5M NaCl, 0.5M AcONa, 10mM ZnSO$_4$, and 5% glycerol, with pH 4.5. The reaction was terminated by phenol treatment; phenol was removed by ether treatment; the resultant DNA was precipitated with ethanol; and the DNA was then dissolved in 19 μl H$_2$O. A mixture containing the DNA (1 μg, 19 μl TEN), T$_4$ DNA ligase (0.9 U, 1 μl TEN), 3mM ATP 3 μl, 50% PEG 6000 (4 μl), and x10 ligation buffer (3 μl) was incubated at 22° C. for 90 min in a final volume of 30 μl. In a similar manner to Example 1, the ligated DNA was introduced into E. coli c 600 $r_k^-m_k^-$ (pCR 712) by transformation. The resultant ampicillin resistant transformants were found to contain plasmid pCR 712. The transformant strain was deposited under the terms of the Budapest Treaty in the FRI (Fermentation Research Institute, Japan) as Accession No. FERM BP-502.

Example 3

Construction of Plsmid pCR 713

The HindIII digest of pCR 701 obtained by the procedure of Example 1 was incubated at 22° C. for 30 min in a total volume 50 μl containing the digest (1 μg, 2 μl TEN), Nuclease S1 (50 U, 1 μl TEN), Nuclease S1 buffer (5 μl), and H$_2$O (42 μl). The composition of the buffer solution was slightly different from that used in Example 2; namely, it consisted of 0.3M AcONa, 0.5M NaCl, and 10mM ZnSO$_4$, with pH 4.6. The reaction was terminated by phenol treatment; phenol was removed by ether treatment; and the DNA was then precipitated with ethanol. A mixture containing the DNA (3 μg, 20 μl TEN), 3mM ATP (8 μl), T$_4$ DNA ligase (3.6 U in 4 μl), and x5 ligation buffer (8 μl) was incubated at 22° C. overnight. The resultant DNA was precipitated with ethanol. As previously described in Example 1, the ligated DNA was introduced into E. coli c 600 $r_k^-m_k^-$ by transformation. The resultant ampicillin resistant transformants, designated as E. coli c 600 $r_k^-m_k^-$ (pCR 713), were found to contain plasmid pCR 713.

Example 4

Construction of Plasmid pCR 714

Plasmid pCR 712 obtained in Example 2 was digested with ClaI by incubation at 37° C. for 2 h in a 50 μl solution containing Plasmid (2 μg, 15 μl), ClaI (18 U, 3 μl), ClaI buffer (5 μl), and H$_2$O 27 μl. The digested DNA was precipitated with ethanol and then dissolved in 41.5 μl of H$_2$O. To this solution was added 20mM dCTP (1.25 μl), 20mM dGTP (1.25 μl), DNA polymerase I (Krenow fragment) (1.5 U, 1 μl TEN), polymerase buffer (5 μl), resulting in a total volume of 50 μl. Incubation continued at 30° C. for 10 min. The reaction was terminated by phenol treatment; phenol was removed by ether extraction; the resultant DNA was precipitated with ethanol; and the precipitate was dissolved in 28 μl of H$_2$O. To this solution was added 3mM ATP (6 μl), T$_4$ DNA ligase (1.8 U, 2 μl) and ligation buffer (4 μl) to make up a final volume of 40 μl. The solution was incubated at 22° C. overnight. The resultant DNA was precipitated with ethanol and the precipitate was dissolved in 40 μl of TEN. As previously described in Example 1, the ligated DNA was introduced into E. coli c 600 $r_k^-m_k^-$ by transformation. The resultant ampicillin resistant transformants, designated as E. coli c 600

$r_k^- m_k^-$ (pCR 714), were found to contain plasmid pCR 714.

Example 5

Expression Experiments

An *E. coli* transformant containing pCR 711, pCR 712, pCR 713 or pCR 714 was grown at 37° C. in LB medium overnight. An 1 ml culture was inoculated onto a fresh M9 medium and grown for 1 h. After addition of 3-β-indoleacrylic acid (15 μg/ml), the culture was incubated for 3 h. *E. coli* cells were grown to a density of $4.0 \times 10^8$ cells per ml. After incubation, the cells were harvested by centrifugation and suspended in 3 ml of PBS buffer (150mM NaCl in 20mM sodium phosphate buffer, pH 7.0) which contains 1 mM PMSF (phenylmethylsulfonyl fluoride). To this suspension was added 250mM EDTA (60 μl) and 30 μl lysozyme (10 mg/l), followed by incubation at 0° C. for 30 min. The resulting spheroplasts were disrupted by sonication and to this was added urea to make up an urea concentration of 8M. The thus-obtained cell lysate was incubated at 37° C. for 1 h. After centrifugation at 30000 rpm for 30 min, the supernatant solution was dialyzed against PBS buffer. The dialysate was applied to the binding competitive radioimmunoassay (see, Nishimori et. al., Gene 19. 337 (1982)).

The above sonicated cell-free extract was treated with 4M urea. After centrifugation the supernatant solution was applied to SDS-polyacrylamide gel electrophoresis. The migrated proteins were blotted onto nitrocellulose filters. Protein bands combined with the prochymosin antibody were detected by autoradiography. For each bacterial extract, a distinctive band corresponding to that of prochymosin was observed. By comparing the density of these protein bands with that of the authentic prochymosin, the amount of prochymosin produced by a specific strain was estimated. The ability of transformed strains containing the expression plasmids was thus in the order of pCR 712 > > pCR 701 > pCR 711 > pCR 714 > pCR 713. As compared to the pCR 701 containing strain, the transformant containing pCR 712 showed the expression efficiency of about twenty five times.

What is claimed is:

1. A recombinant expression plasmid comprising the full cDNA sequence of prochymosin and an *E. coli* trp promoter-operator system and capable of expressing the full-length cDNA of prochymosin under the control of the trp promoter, characterized in that an ATG initiation codon is joined to the N-terminus of said cDNA and that the base pairs between the SD sequence and the ATG initiation codon are

GTATCGAT
CATAGCTA.

2. *E. coli* 600 $r_k^- m_k^-$ (pCR 712) as designated Accession No. FERM-BP-502.

3. Plasmid pCR 712 found in *E. coli* deposited in the FRI as FERM-BP-502.